United States Patent
Schomberg

(10) Patent No.: US 7,688,937 B2
(45) Date of Patent: Mar. 30, 2010

(54) THREE DIMENSIONAL ELECTRON BEAM COMPUTED TOMOGRAPHY

(75) Inventor: Hermann Schomberg, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 68 days.

(21) Appl. No.: 11/568,320

(22) PCT Filed: Apr. 18, 2005

(86) PCT No.: PCT/IB2005/051252

§ 371 (c)(1),
(2), (4) Date: Oct. 26, 2006

(87) PCT Pub. No.: WO2005/104952

PCT Pub. Date: Nov. 10, 2005

(65) Prior Publication Data

US 2007/0165773 A1     Jul. 19, 2007

(30) Foreign Application Priority Data

Apr. 28, 2004 (EP) ................................. 04101786

(51) Int. Cl.
*G01N 23/083* (2006.01)
(52) U.S. Cl. ............................... 378/10; 378/17; 378/19
(58) Field of Classification Search .................. 378/10, 378/17, 19
See application file for complete search history.

(56) References Cited

U.S. PATENT DOCUMENTS

| | | | |
|---|---|---|---|
| 4,352,021 A | 9/1982 | Boyd et al. | |
| 4,672,649 A | 6/1987 | Rutt | |
| 5,712,889 A | 1/1998 | Lanzara et al. | |
| 5,757,878 A | 5/1998 | Dobbs et al. | |
| 6,047,040 A | 4/2000 | Hu et al. | |
| 6,130,929 A | 10/2000 | Saha | |

(Continued)

FOREIGN PATENT DOCUMENTS

WO    WO 03051201 A2    6/2003

OTHER PUBLICATIONS

Defrise, M., et al.; A Cone-Beam Reconstruction Algorithm Using Shift-Variant Filtering and Cone-Beam Backprojection; 1994; IEEE-Trans. Med. Image; 13(1)186-195.

(Continued)

*Primary Examiner*—Edward J Glick
*Assistant Examiner*—Thomas R Artman

(57) ABSTRACT

An electron beam computed tomography system is provided that uses a cone beam geometry to generate truly three-dimensional images. The required cone beam projections can be obtained using a single sweep of the electron beam along the target ring (20). The target ring (20) is non-planar and shaped roughly like a ⅝th segment of the boundary curve of a saddle. The resulting source trajectory satisfies Tuy's completeness condition with respect to a sizeable volume of interest around the isocenter of the system. The detector (28) has a large area and is built from a plurality of small, brick-shaped detector modules (32), which are placed side by side along a detector trajectory that is a mirror image, through the isocenter, of the source trajectory. Owing to the special shapes of the target ring and the detector strip, a cone-beam of x-rays starting from the target ring and heading towards the opposite segment of the detector strip is not blocked by other portions of the detector.

20 Claims, 5 Drawing Sheets

U.S. PATENT DOCUMENTS

| | | |
|---|---|---|
| 6,628,745 B1 | 9/2003 | Annis et al. |
| 7,020,232 B2 * | 3/2006 | Rand et al. ..................... 378/4 |
| 7,167,538 B2 * | 1/2007 | Strobel et al. ................. 378/17 |
| 7,342,992 B2 * | 3/2008 | Schomberg .................. 378/19 |
| 2002/0094064 A1 | 7/2002 | Zhou et al. |
| 2002/0168053 A1 | 11/2002 | Schomberg |
| 2003/0161434 A1 | 8/2003 | Rand et al. |
| 2005/0111610 A1 * | 5/2005 | De Man et al. ............... 378/10 |

OTHER PUBLICATIONS

Schomberg, H.; Complete Source Trajectories for C-Arm Systems and a Method for Coping with Truncated Cone-Beam Projections; 2001; Proc. Int'l Mtg on Fully Three-Dimensional Image Reconstruction in Radiology and Nuclear Medicine; pp. 221-224.

* cited by examiner

THREE DIMENSIONAL ELECTRON BEAM COMPUTED TOMOGRAPHY

The present invention relates to computed tomography. More specifically, the present invention relates to a computed tomography apparatus, in particular to an electron beam computed tomography apparatus, to a method of operating such an apparatus, and to a computer program for operating such an apparatus.

In a conventional electron beam computed tomography system, such as described in U.S. Pat. No. 4,352,021, an electron beam is produced by an electron gun and is accelerated downstream along the z-axis of an evacuated chamber. Further downstream, a system of electromagnetic coils focuses and reflects the electron beam about 30 degrees into a semi-circular scanning path. The deflected beam strikes a target ring made of a suitable material, such as tungsten. A cone beam of x-rays emanates from the point where the electron beam hits the target ring. This cone beam of x-rays is collimated to a transverse fan beam by means of a collimator.

The fan beam of x-rays penetrates a transverse slice of an object, such as a patient that is disposed along the z-axis. The x-rays pass through the scanned slice of the object and are attenuated by various amounts, depending upon the x-ray density within the object. A curved row of x-ray detectors arranged on the opposite side of the object intercepts the transmitted and attenuated fan beam of x-rays, thus providing a fan beam projection of the scanned slice of the object. By steering the electron beam along the target ring, fan beam projections of the same transverse slice of the object are obtained from a large number of azimuthal angles. The measured fan beam projections are then processed into a two-dimensional image that represents the x-ray density distribution of the scanned transverse slice of the object. The processing is done by a computer that executes a suitable reconstruction algorithm. To allow for a good image quality, the azimuthal range of the projection angles must span at least 180 degrees plus the angle of the fan beam. The opposite detector row must span an even greater azimuthal angle. Therefore, it is not possible to place the target ring and the detector row in the same transverse slice. In U.S. Pat. No. 4,352,021, this problem is solved by means of a small axial offset between the plane containing the target ring and the plane containing the detector row. This axial offset, however, creates some level of artifacts in the reconstructed image of the scanned slice. This disadvantage is out-weighed by the ultra-fast speed of the scanning process. For example, a set of fan beam projections that allows a fairly good reconstruction of a slice of an object may be collected within 50 milliseconds. A three-dimensional image of a slab of an object may be obtained by stacking two-dimensional images. The apparatus described in U.S. Pat. No. 4,352,021 allows for the scanning of a small number of adjacent slices without mechanically moving the object. Imaging a substantial three-dimensional volume, however, requires stepping the object and, therefore, takes a relatively long time.

In U.S. Pat. App. No. 2003/0161434 A1 it is proposed to overcome the problem with the axial offset between the target ring and the detector row by giving both a helical shape, or by tilting both slightly. This approach requires a longitudinal translation of the object during the scan process. Collecting the data for a three-dimensional image of an object is, therefore, still relatively time consuming.

It is an object of the present invention to provide a computed tomography apparatus that allows for the ultra-fast collection of a set of data from which an accurate three-dimensional image of an object may be reconstructed.

According to an exemplary embodiment of the present invention, a computed tomography apparatus is provided, comprising a source of radiation that emits a cone beam of radiation from a first location. The cone beam of radiation penetrates a volume of interest around a distinguished point in space, the isocenter, that is conceptually attached to the computed tomography apparatus. The source of radiation is adapted such that the first location is displaceable along a first trajectory. Furthermore, a radiation detector strip is provided. The center line of the radiation detector strip extends along a second trajectory. The center line of the detector strip is obtained, essentially, by mirroring the first trajectory through the isocenter of the computed tomography apparatus. According to an aspect of this exemplary embodiment of the present invention, the first and second trajectories are both non-planar and curved in such a way that a cone beam that emanates from a point of the first trajectory towards the opposite portion of the detector strip is not significantly blocked by any other portion of the detector strip. In addition, the first trajectory is curved such that it may satisfy Tuy's completeness condition with respect to a sizeable volume around the isocenter. The satisfaction of this completeness condition makes it possible to reconstruct a faithful image of the object within this volume.

According to another exemplary embodiment of the present invention, the source of radiation is implemented by an electron source for generating an electron beam that is steered along a target ring. The center line of the target ring has the curvature of the first trajectory. According to this exemplary embodiment of the present invention, three-dimensional electron beam computed tomography may be performed with no mechanically moving parts.

According to yet another exemplary embodiment of the present invention, the radiation beam is a cone beam of x-rays.

According to yet another exemplary embodiment of the present invention, collimating means are provided to block portions of the cone beam of radiation, typically those portions that cannot hit the detector strip. The collimator means can be a collimator slit that sits near the target ring and is curved essentially like the first trajectory.

According to yet another exemplary embodiment of the present invention, the detector strip is built from a plurality of detector modules. Each of these modules is in itself a two-dimensional array of small detector elements. According to this exemplary embodiment of the present invention, every other detector module is promoted to a slightly larger isocentric sphere, in other words, adjacent detector modules are alternately arranged at two slightly different distances from the isocenter. This arrangement makes it possible to place the detector modules so close together that an observer looking from the tip of a cone beam sees no gaps between the detector modules.

According to yet another exemplary embodiment of the present invention, the first and second trajectories extend on surfaces of two isocentric spheres of different radii.

According to yet another exemplary embodiment of the present invention, a method of operating a computed tomography apparatus is provided, wherein a source of radiation is provided for generating a cone beam of radiation that is emitted from a displaceable first location. This source of radiation is operated such that the first location is displaced along a first trajectory, and a radiation detector strip is provided whose center line extends along a second trajectory. The two trajectories are both non-planar and curved in such a way that a cone beam that emanates from a point of the first trajectory towards the opposite portion of the detector strip is not significantly blocked by any other portion of the detector strip. In particular, during operation, i.e. during a scan, no portion of the radiation detector blocks the radiation beam.

A further exemplary embodiment of the method of operating a computed tomography apparatus is provided in claim 8.

Advantageously, according to the present invention, a very fast, three-dimensional computed tomography system is provided that allows for the very fast cone beam scanning of a sizeable volume, large enough to contain a human heart, and the subsequent faithful reconstruction of the spatial distribution of the x-ray density within this volume.

The present invention relates furthermore to a computer program for operating a computed tomography apparatus. The computer program according to the present invention is set forth in claim 9. The computer program according to the present invention may preferably be loaded into a working memory of a controller which controls the operation of the computed tomography apparatus. The computer program causes the computer tomography apparatus to perform the method of the present invention. The computer program may be stored on a computer readable medium, such as a CD-ROM. The computer program may also be presented over a network, such as the world wide web, and may be downloaded into the working memory of a controller from such a network. The computer program may be written in any suitable programming language, such as C++.

It may be seen as a gist of the present invention that a target ring and a radiation detector strip of a scanning electron beam computed tomography apparatus are shaped in such a way that they do not block each other and at the same time allow for the collection of a "complete" set of cone-beam projections of a sizeable volume of interest, large enough to contain a human heart. Furthermore, an electron beam computed tomography apparatus is provided that is capable of collecting the data required for a three-dimensional image of an object without moving the object to be imaged, using only a single sweep of the electron beam along the target ring. This goal is achieved by using a cone beam of x-rays, rather than a fan beam. The one-dimensional, curved detector row of a conventional electron beam computed tomography apparatus is replaced by a two-dimensional, curved detector strip. The reconstruction is achieved by a suitable cone beam reconstruction algorithm. Target ring and detector strip have very peculiar shapes that make it possible to achieve a fairly good image quality within the volume of interest.

These and other aspects of the present invention are apparent from and will be elucidated with reference to the embodiments described hereinafter and with reference to the following drawings.

Figure 1:
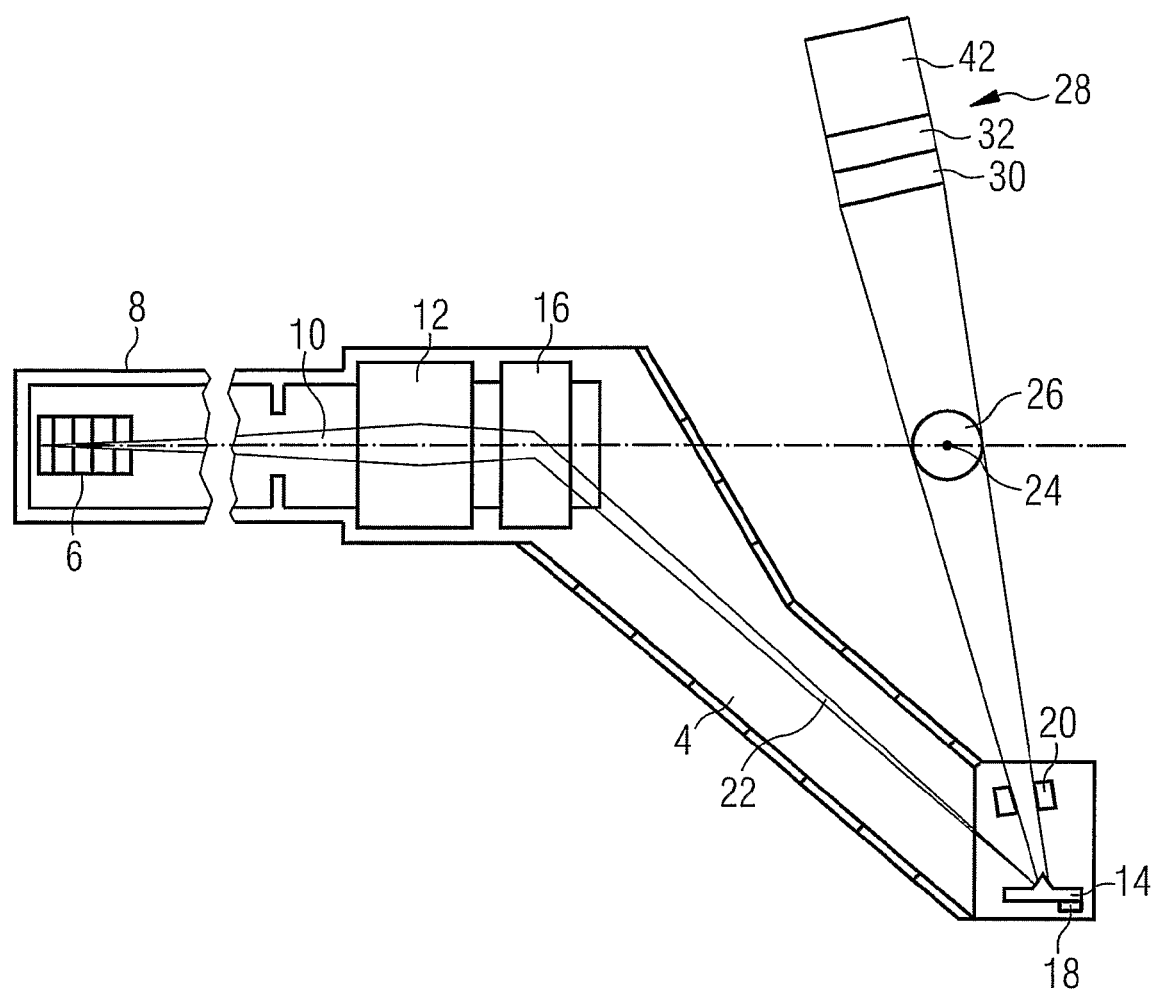
FIG. 1 is a simplified schematic cross-sectional view of an exemplary embodiment of an electron beam computed tomography apparatus according to the present invention.

FIG. 1 shows a cross-sectional view of an exemplary embodiment of an electron beam computed tomography apparatus. The apparatus depicted in FIG. 1 comprises an electron beam tube 2, which includes a vacuum envelope 4, which houses an electron gun 6 at the cylindrical end 8. The electron gun 6 projects an axial electron beam 10 along the cylindrical portion. Focusing coils 12 and bending coils 16 are provided for focusing the electron beam and steering the focused electron beam along the target ring 14. The bending coils 16 are controlled by a suitable controller such that the electron beam rapidly sweeps along the source trajectory.

The target ring 14 is made of a suitable material, for example, tungsten, such that a cone beam of x-rays emanates from the point where the electron beam strikes the target ring. The center line of the target ring 14 will also be referred to as the source trajectory. The source trajectory is non-planar and curved in a special way, as will be described in further detail with respect to the following drawings.

The target ring 14 may be associated with a suitable cooling coil 18 which is arranged to cool the target ring.

The apparatus has a distinguished center point, the isocenter 24. The arrangement of the electron beam 22 and the target ring 14 is such that the axis of the cone beam emanating from a point on the target ring points towards the isocenter 24. Furthermore, the apparatus has a radiation detector arrangement 28, which is opposite to the target ring 14. Only a cross-sectional view of the radiation detector arrangement 28 is depicted in FIG. 1. The apparatus is intended to acquire transversely non-truncated cone beam projections of a certain volume of interest 26 around the isocenter 24. The volume of interest 26 is large enough to contain a human heart, for example.

Reference character 20 designates a collimator which is disposed near the target ring 14 and between the target ring 14 and the radiation detector arrangement 28. The collimator 20 blocks x-rays that cannot hit the radiation detector arrangement 28.

The radiation detector arrangement 28 is built from multiple copies of a detector module 32. Each module has a flat, rectangular sensitive area, which is covered with an anti-scatter grid 30. The detector electronics may be placed in a compartment 42 behind the sensitive area.

The sensitive area of each detector module faces the target ring. Moreover, the straight line starting at the center point of the sensitive area and passing through the isocenter meets the target ring. The anti-scatter grid 30 is focused on this meeting point.

The detector modules are placed side by side so that their sensitive areas form a strip. The center line of this strip will be referred to as the detector trajectory. The detector trajectory is also non-planar and curved in a special way. Specifically, every straight line that starts from a point on the source trajectory and passes through the isocenter meets the detector trajectory. Thus, the detector trajectory is a mirror image, through the isocenter, of the source trajectory. Actually, however, the detector, trajectory is a little longer than this mirror image of the source trajectory. The reason for this will be explained further below.

According to a preferred embodiment of the present invention, the source trajectory and the detector trajectory extend on surfaces of spheres that are both centered at the isocenter 24. However, the diameter of the sphere on which the source trajectory is located is slightly larger than the diameter of the sphere on which the detector trajectory is located.

The same reference numerals will be used in the following description of FIGS. 2-14 to designate the same or corresponding elements.

Figure 2:
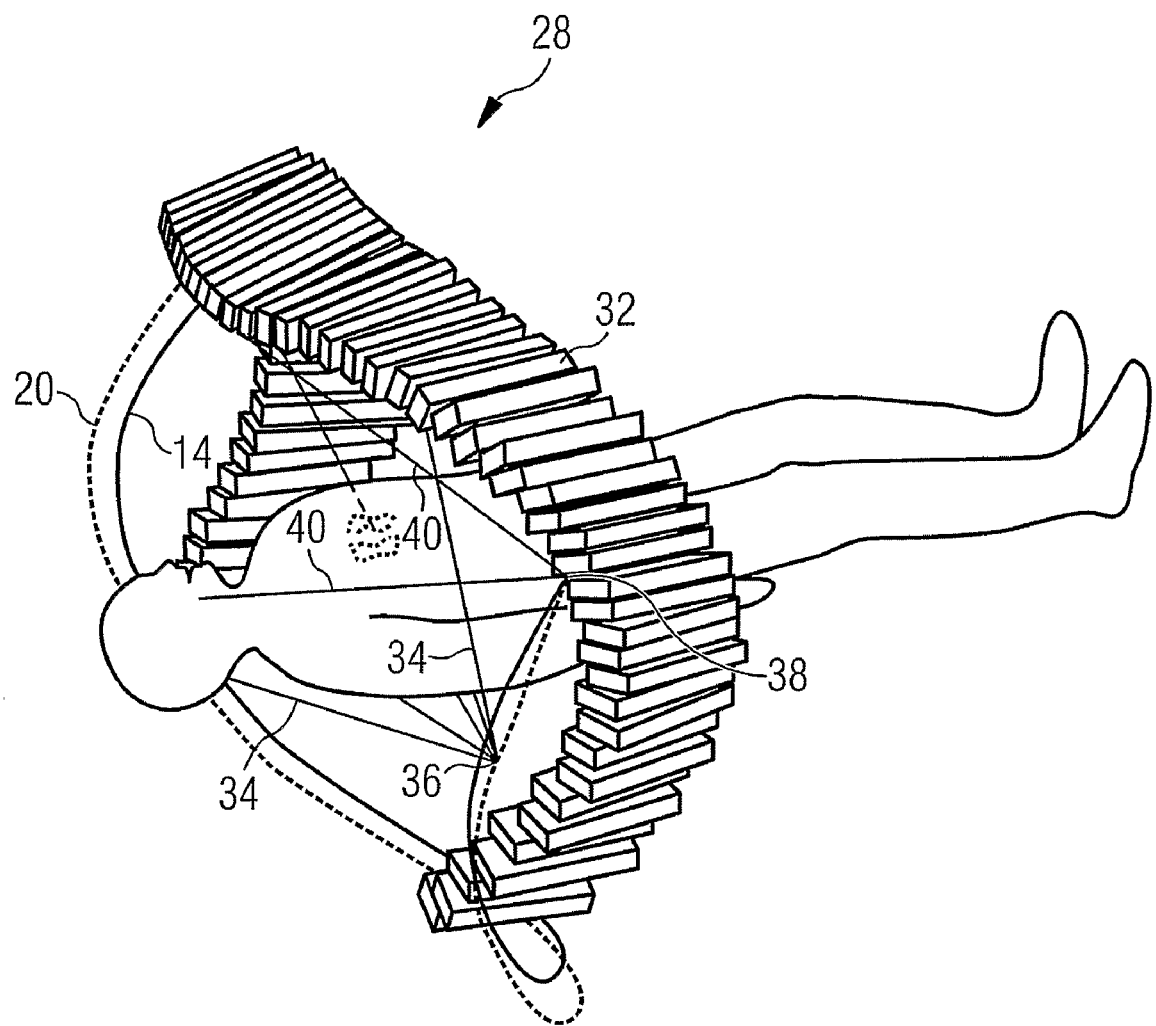
FIG. 2 shows a schematic three-dimensional representation of the source/detector arrangement of the system of FIG. 1.

FIG. 2 shows a simplified perspective view of the arrangements of the radiation detector arrangement 28 and the target ring 14 according to an exemplary embodiment of the present invention as used in the system of FIG. 1. In FIGS. 2-6, the target ring is depicted as a dotted line. The detector modules are indicated by brick-shaped cubicles.

As may be taken from FIG. 2, the source trajectory defined by the target ring 14 extends on the surface of an isocentric sphere and resembles a portion of the boundary curve of a saddle.

As may also be taken from FIG. 2, a plurality of brick-shaped detector modules 32 are arranged along a non-planar trajectory that extends on the surface of an isocentric sphere. However, the diameter of the sphere on which the source trajectory is located is slightly larger than the diameter of the sphere on which the detector trajectory is located. The detector trajectory defined by the detector arrangement 28 also resembles a portion of the boundary curve of a saddle. With each module, the straight line starting at the center point of the sensitive area of this module and passing through the isocenter meets the source trajectory.

As may also be taken from FIG. 2, the collimator 20 is a slit whose center line, the collimator trajectory, extends essentially parallel to the target ring 14. Thus, the collimator trajectory is essentially a scaled image of the source trajectory. Actually, however, the collimator trajectory is a little longer than this scaled image of the source trajectory. The reason for this will be explained further below.

The exemplary source/detector arrangement depicted in FIG. 2 has two important properties. First, a cone beam emanating from a point on the source trajectory and directed towards the opposite portion of the detector strip is not blocked by any other portion of the detector strip. This is illustrated by lines 34 and 40 in FIG. 2, which indicate two cone beams starting from locations 36 and 40 near the ends of the target ring 14. Second, the source trajectory defined by the target ring 14 is complete (in the sense of Tuy) with respect to a sizeable volume around the isocenter. In this context, a source trajectory is said to be complete with respect to a volume V, if every plane that intersects V also intersects the source trajectory. A planar source trajectory cannot be complete with respect to a true volume. If a source trajectory is complete with respect to V, then an accurate, three-dimensional image of the content of V may be reconstructed from the cone beam projections of V taken along the source trajectory, provided these cone beam projections are not truncated. The reconstruction may be achieved by one of several known cone beam reconstruction algorithms, for example, by the cone beam filtered backprojection algorithm described in M. Defrise et al. "A cone-beam reconstruction algorithm using shift-variant filtering and cone-beam backprojection", IEEE—Trans. Med. Image, 13 (1): 186-195, March 1994, which is hereby incorporated by reference. If the object to be imaged is a human being, however, the cone beam projections will be axially truncated, though not transversely. In this case, it is advisable to extend the truncated projections prior to the reconstruction. A suitable extension method is described in H. Schomberg, "Complete source trajectories for C-arm systems and a method for coping with truncated cone-beam projections," in Proceedings of the 2001 International Meeting on Fully Three-Dimensional Image Reconstruction in Radiology and Nuclear Medicine, Pacific Grove, Calif., Oct. 30-Nov. 2, 2001, pp. 221-224, which is hereby incorporated by reference. The volume of interest 26 could be chosen, for example, as the biggest isocentric ball with respect to which the source trajectory is complete.

Advantageously, the above described arrangement of target ring 14 (source of radiation) and detector arrangement 28 allows for the acquisition of a "complete" set of cone beam projections of a sizeable volume, large enough to contain an entire human heart. A single cone beam projection is acquired by activating a segment of the detector strip that is opposite to the point where the electron beam currently strikes the target ring. The activated segment should be so wide that the cone beam projection is not transversely truncated. However, due to the limited axial extent of the detector strip, the cone beam projection may be axially truncated. A series of cone beam projections is acquired by repeating this process while the electron beam sweeps along the target ring 14. A single sweep suffices. This allows for a very fast scanning time in the range of only 50 milliseconds. The collimator slit 20 is shaped such that it lets pass, approximately, only those portions of the cone beam of x-rays that can hit the opposite detector strip.

Figure 3:
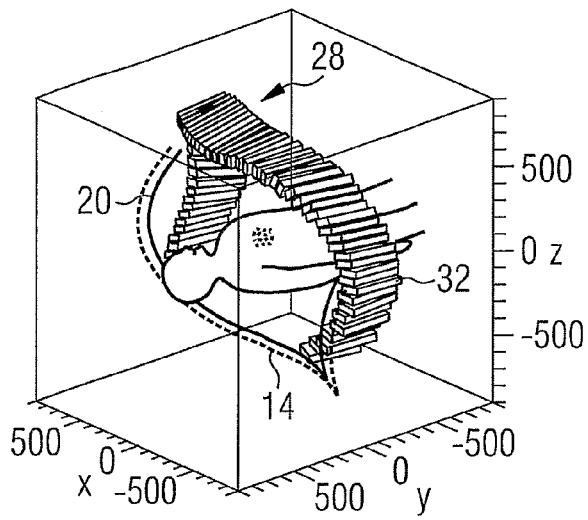
FIG. 3 shows another three-dimensional schematic representation of the source/detector arrangement of the system of FIG. 1.
Figure 4:
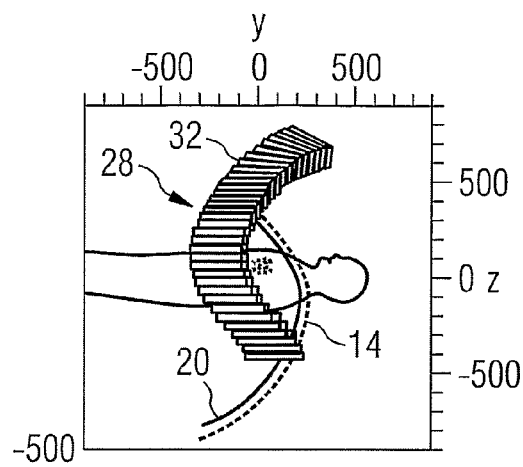
FIG. 4 shows a side view of the arrangement of FIG. 3.
Figure 5:
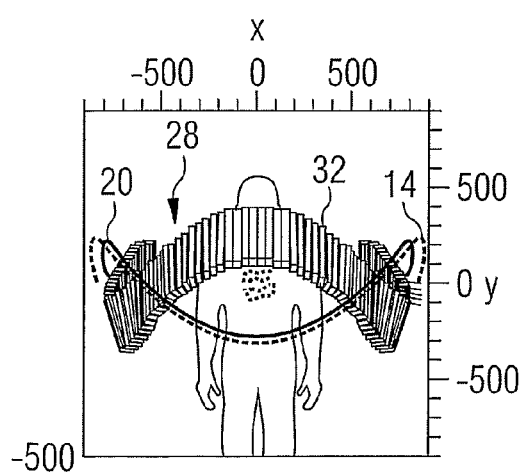
FIG. 5 shows a top view of the arrangement of FIG. 3.
Figure 6:
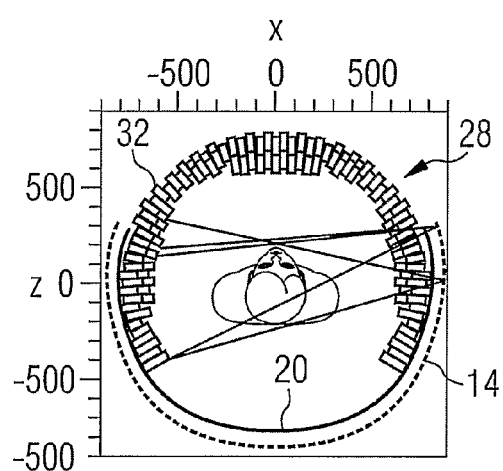
FIG. 6 shows a front view of the arrangement of FIG. 3.

FIG. 3 shows a section of the exemplary source/detector arrangement from the same perspective as FIG. 2. FIGS. 4-6 show this section from the side, the top, and the front, respectively.

As apparent from FIG. 6, when seen from the front, the detector strip and the target ring do overlap. Nevertheless, as can be seen from FIGS. 4 and 5, owing to the special curvatures of the target ring and the detector strip, no cone beam emanating from a point on the target ring and directed towards the opposite portion of the detector strip is blocked by any other portion of the detector strip.

It is also apparent from these figures that the detector modules are alternately arranged at two slightly different distances from the isocenter. This will be further explained below.

In the following, the geometrical aspects of the source/detector arrangement of FIGS. 2-6 are described in further detail. This will be done by specifying a number of prominent points and curves of the objects involved. This, in turn, will be done using a methodology described in the aforementioned article by Schomberg. This methodology uses two Cartesian two coordinate systems, respectively called the "base frame" and the "tool frame." The origin of the base frame is located at the isocenter of the scanner. The y-axis of the base frame points horizontally from the isocenter to the far end of a patient table attached to the apparatus, and the z-axis points vertically upwards. The x-axis complements the other two axes so as to form a right-handed Cartesian coordinate system.

The tool frame has the same origin as the base frame and may assume arbitrary orientations with respect to the base frame. A specific orientation is characterized by three angles $\theta_k$, k=1,2,3. The definition of these angles is in part subject to conventions. A point represented by $r^{(t)}=(x^{(t)}, y^{(t)}, z^{(t)})$ in the tool frame is represented by $r^{(b)}=(x^{(b)}, y^{(b)}, z^{(b)})$ in the base frame, where $$r^{(b)}=R(\theta_1,\theta_2,\theta_3)r^{(t)} \qquad (1)$$

for some 3×3 rotation matrix $R(\theta_1, \theta_2, \theta_3)$. Using the conventions for the definition of the angles in the aforementioned article by Schomberg, the matrix $R(\theta_1, \theta_2, \theta_3)$ is given by $$R(\theta_1, \theta_2, \theta_3) = \begin{pmatrix} c_1c_2c_3 - s_1s_3 & -c_1c_2s_3 - s_1c_3 & c_1s_2 \\ s_1c_2c_3 + c_1s_3 & -s_1c_2s_3 + c_1c_3 & s_1s_2 \\ -s_2c_3 & s_2s_3 & c_2 \end{pmatrix} \quad (3)$$

with $c_k = \cos\theta_k$ and $S_k = \sin\theta_k$, k=1,2,3.

The angles $\theta_k$ may be replaced by functions $\theta_k(\lambda)$ defined in some interval $\Lambda$. Then, as $\lambda$ varies, the point represented by $r^{(t)}$ in the tool frame describes the trajectory represented by $$r^{(b)}(\lambda) = R(\theta_1(\lambda), \theta_2(\lambda), \theta_3(\lambda)) r^{(t)}, \lambda \in \Lambda, \quad (2)$$

in the base frame. Since $R(\theta_1(\lambda), \theta_2(\lambda), \theta_3(\lambda))$ is a rotation matrix, the trajectory described by the point $r^{(b)}(\lambda)$ is confined to the centered sphere with radius $\|r^{(t)}\|$.

To obtain the prominent points and curves in the base frame, one (i) defines a number of "master points" in the tool frame; (ii) chooses suitable functions $\theta_k(\lambda)$, k=1,2,3; (iii) invokes the methodology in the aforementioned article by Schomberg to obtain a "source trajectory" in the base frame that defines the center line of the target ring; (iv) invokes this methodology to obtain a "detector trajectory" in the base frame and follows a recipe for placing detector modules along this detector trajectory; and (v) invokes this methodology to define a "collimator trajectory" in the base frame and follows a recipe for deriving the boundary curves of the collimator slit from the collimator trajectory and the desired local width of the slit.

Figure 7:
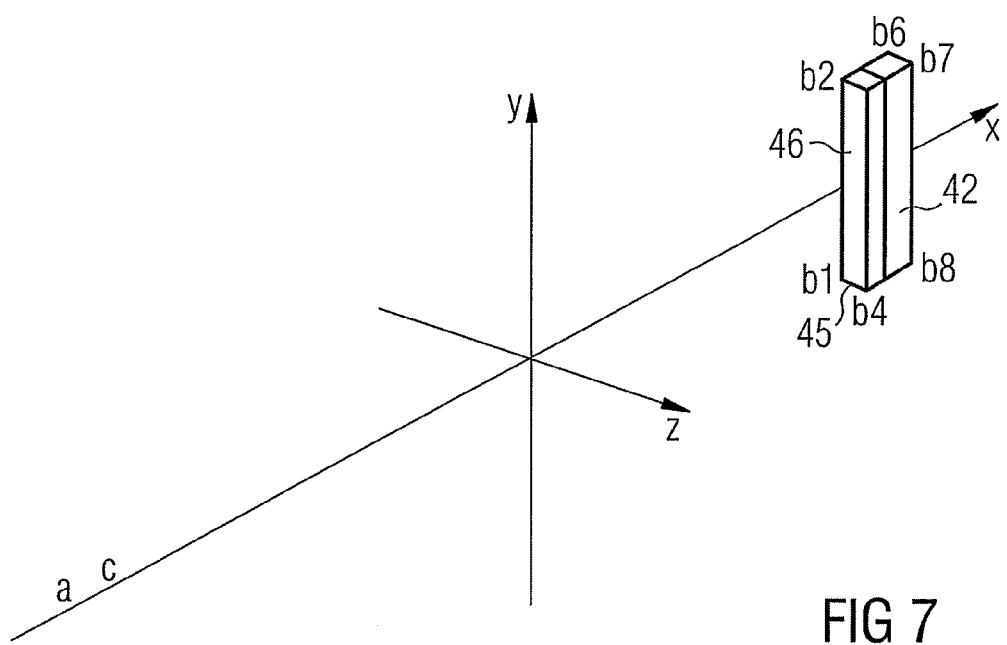
FIG. 7 shows a three-dimensional coordinate system for further explaining the present invention.

The master points in the tool frame are a "master source point" a; a "master detector point" b; the 8 vertices $b_1, \ldots b_8$ of a "master detector brick" 45, and a "master collimator point" c. These points are depicted in FIG. 7. The master detector brick 45 is a brick-shaped volume of space that is just large enough to hold a detector module 32. The sensitive area of the detector module then corresponds to the face 46 defined by points $b_1$-$b_4$.

The coordinates of the points a, b and c depend on six parameters $r_s$, $r_d$, $r_c$, $w_b$, $l_b$, $h_b$. These parameters $r_s$, $r_d$, $r_c$ represent the distances between the isocenter and the points a, b and c, respectively. The parameters $w_b$, $l_b$, $h_b$ represent the width, length, and height of the master detector brick 45. The master source point is $$a = -(r_s, 0, 0).$$

The master detector point is $$b = (r_d, 0, 0) = -\frac{r_d}{r_s}a.$$

The eight vertices of the master detector brick are as follows:

$$b_1 = (r_d, -l_b/2, -w_b/2), \quad (6)$$

$$b_2 = (r_d, -l_b/2, -w_b/2), \quad (7)$$

$$b_3 = (r_d, -l_b/2, -w_b/2), \quad (8)$$

$$b_4 = (r_d, -l_b/2, -w_b/2), \quad (9)$$

$$b_5 = b_1 + (h_b, 0, 0), \quad (10)$$

$$b_6 = b_2 + (h_b, 0, 0), \quad (11)$$

$$b_7 = b_3 + (h_b, 0, 0), \quad (12)$$

$$b_8 = b_4 + (h_b, 0, 0), \quad (13)$$

The master collimator point is $$c = -(r_c, 0, 0) = \frac{r_c}{r_s}a.$$

The functions $\theta_k(\lambda)$, k=1,2,3 are defined in a "master interval" of the form $$\Lambda = [-\epsilon, 1+\epsilon],$$

where $\epsilon \geq 0$ is a parameter. When designing the target ring, the detector strip and the collimator slit, these functions are restricted to the following intervals:

$$\Lambda_s = [0,1], \Lambda_d = [-\epsilon_d, 1+\epsilon_d], \Lambda_c = [-\epsilon_c, 1+\epsilon_c], \quad (18)$$

where $\epsilon_d$ and $\epsilon_c$ are further parameters with $0 < \epsilon_d$, $\epsilon_c \leq \epsilon$. The reason behind making $\Lambda_d$ and $\Lambda_c$ a little wider than $\Lambda_s$, will be described further below.

Figure 8:
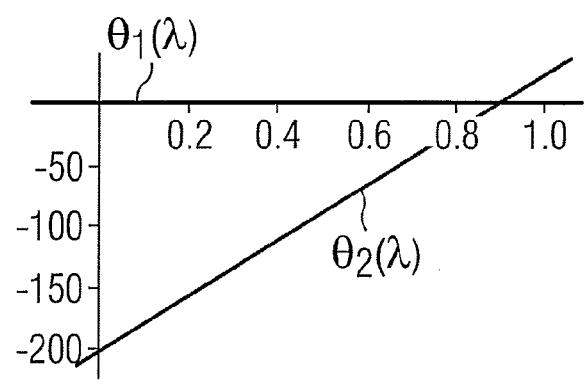
FIG. 8 shows a graph used for generating the source/detector arrangement shown in FIGS. 2 and 3 according to an exemplary embodiment of the present invention.
Figure 9:
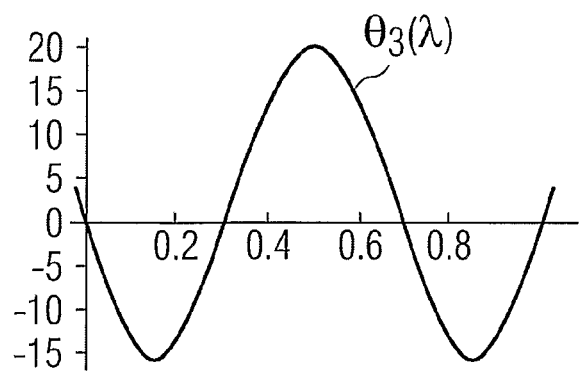
FIG. 9 shows another graph used for generating the source/detector arrangement shown in FIGS. 2 and 3 according to an exemplary embodiment of the present invention.

FIGS. 8 and 9 depict the graphs of the three functions $\theta_1(\lambda)=0$, $\theta_2(\lambda)=-200+220\lambda$, and $\theta_3(\lambda)$ that have been used to generate FIGS. 2-6, as further described below. The function $\theta_3(\lambda)$ admits of no closed form expression, but may be specified in tabular form. The function values represent angles, measured in degrees.

The source trajectory is defined by $$a(\lambda) = R(\theta_1(\lambda), \theta_2(\lambda), \theta_3(\lambda))a, \lambda \in \Lambda_s. \quad (19)$$

With the functions $\theta_1(\lambda)$, $\theta_2(\lambda)$, and $\theta_3(\lambda)$ chosen as depicted in FIGS. 8 and 9, this source trajectory is symmetric about the "sagittal" plane x=0. Moreover, this source trajectory is complete with respect to sizeable ball around the isocenter, large enough to hold a human heart. The completeness may be checked using, for example, a method described in the aforementioned article by Schomberg.

The geometry of the detector arrangement 28 is described in the following. The detector trajectory is defined by:

$$b(\lambda) = R(\theta_1(\lambda), \theta_2(\lambda), \theta_3(\lambda))b, \lambda \in \Lambda_d. \quad (20)$$

Since b=−const a for some positive constant const, the detector trajectory is a scaled mirror image of the source trajectory.

A recipe for placing detector modules along the detector trajectory is described next. First, define the eight trajectories $$b_j(\lambda) = R(\theta_1(\lambda), \theta_2(\lambda), \theta_3(\lambda))b_j, \lambda \in \Lambda_d, j=1, \ldots, 8 \quad (21)$$

Given $\lambda \in \Lambda$, the "detector brick" $B(\lambda)$ is formed by the eight points $b_1(\lambda), \ldots, b_8(\lambda)$. The detector brick $B(\lambda)$ represents a volume of space that is just large enough to contain a detector module. The sensitive area of a detector module contained in a detector brick $B(\lambda)$ corresponds to the face formed by the four points $b_1(\lambda), \ldots, b_4(\lambda)$. The center point of the sensitive area corresponds to the point $b(\lambda)$. The straight line that connects $b(\lambda)$ with the isocenter, which equals the origin of the base frame, is perpendicular to the sensitive area and meets the source trajectory at the point $a(\lambda)$.

Next, a recipe for placing detector bricks along the detector trajectory is presented. The first detector brick to be placed is $B(\lambda_0)$ with $\lambda_0=0.5$. The second detector brick is $B(\lambda_1)$ with $\lambda_1 > \lambda_0$ and such that $B(\lambda_1)$ just touches $B(\lambda_0)$. The third detector brick is $B(\lambda_2)$ with $\lambda_2 > \lambda_1$ and such that $B(\lambda_2)$ just touches $B(\lambda_1)$. Continuing in this way, one finds a sequence $\lambda_0 < \lambda_1 < \ldots < \lambda_M < 1+\epsilon_d$, such that $B(\lambda_m)$ just touches $B(\lambda_{m-1})$ for m=1, 2, ..., M and no $\lambda_{M+1}$ can be found such that $\lambda_{M+1} < 1+\epsilon_d$ and $B(\lambda_M)$ just touches $B(\lambda_{M-1})$. In a similar fashion, one finds a sequence $\lambda_0 > \lambda_{-1} > \ldots > \lambda_{-M'} \geq 1-\epsilon_d$, such that $B(\lambda_m)$ just touches $B(\lambda_{m-1})$ for m=-1, -2, ..., -M' and no $\lambda_{M'-1}$ can be found such that $\lambda_{-M'-1} \geq -\epsilon_d$ and $B(\lambda_{M'})$ just touches $B(\lambda_{-M'-1})$. In the preferred case of a detector trajectory that is symmetrical with respect to the sagittal plane x=0, one will have M=M' and $\lambda_{-m}=\lambda_m$ for m=1, 2, . . . , M. Finally, for the physical realization of the detector strip, the volumes represented by the detector bricks just found are filled with detector modules.

The detector bricks thus found are not parallel, however. As a result, an observer looking from the source trajectory towards the detector strip will see small, wedge-shaped gaps between adjacent detector modules. These gaps would cause corresponding gaps in the measured cone beam projections, which would in turn degrade the achievable image quality.

According to one aspect of the present invention, the observed gaps between adjacent detector modules are removed by first promoting every other detector brick (module) to a slightly larger isocentric sphere and then shifting all detector bricks (modules) as close together as possible. The resulting arrangement is illustrated in FIG. 6. The newly arranged detector modules are still not parallel, but if the radius of the larger isocentric sphere is large enough, an observer looking from the source trajectory towards the detector strip will no longer see gaps between adjacent detector bricks. Instead, the "near" detector bricks will cast shadows on the "far" detector modules, but this will cause no gaps in the measured cone beam projections.

Figure 10:
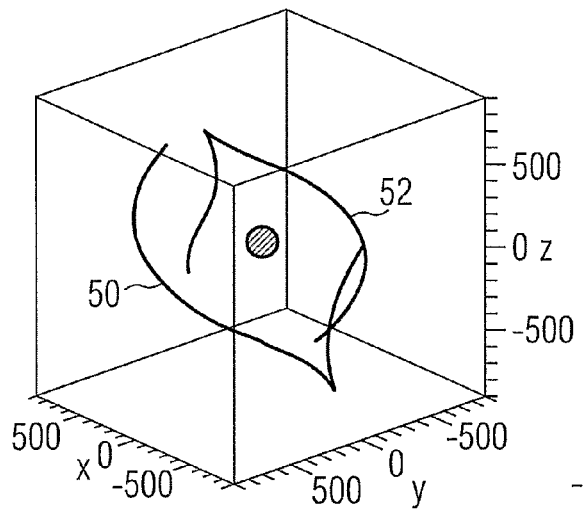
FIG. 10 shows a simplified perspective view of the arrangement depicted in FIG. 3.
Figure 11:
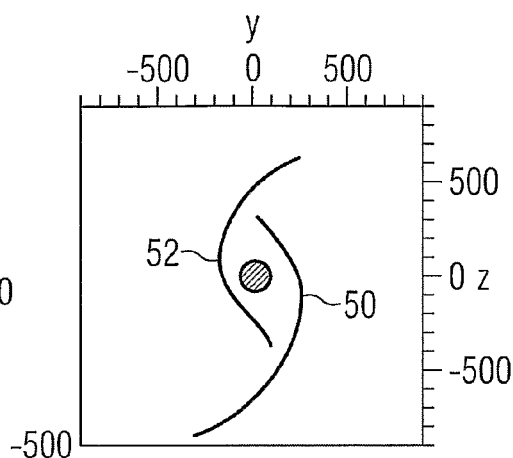
FIG. 11 shows a side view of the arrangement of FIG. 10.
Figure 12:
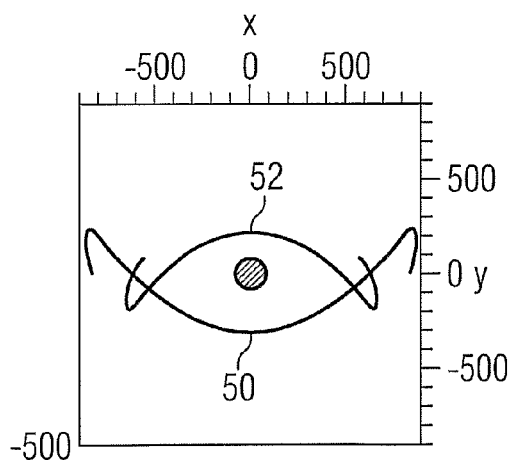
FIG. 12 shows a top view of the arrangement of FIG. 10.
Figure 13:
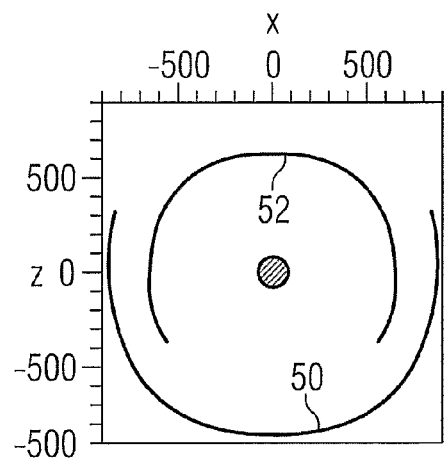
FIG. 13 shows a front view of the arrangement of FIG. 10.

FIG. 10 shows a perspective view of the source trajectory 50 and the detector trajectory 52. FIGS. 11, 12, and 13 show a side view, a top view, and a front view of the same trajectories. From the side view 11, it can be seen that the detector trajectory "stays away" from the source trajectory. It is this property of the two trajectories that allows for what might be called a non-self-blocking source/detector arrangement.

The collimator trajectory is defined by $$c(\lambda) = R(\theta_1(\lambda), \theta_2(\lambda), \theta_3(\lambda))c, \lambda \in \Lambda_c \quad (22)$$

Since c=const a for some positive constant const, the collimator trajectory is a scaled image of the source trajectory. The collimator slit itself is defined by its two boundary curves. These boundary curves are defined with the help of the collimator trajectory and two further functions $w_1(\lambda)$ and $w_2(\lambda)$ according to $$c_1(\lambda) = c(\lambda) - R(\theta_1(\lambda), \theta_2(\lambda), \theta_3(\lambda))(0,0,w_1(\lambda)), \lambda \in \Lambda_c, \quad (23)$$

$$c_1(\lambda) = c(\lambda) + R(\theta_1(\lambda), \theta_2(\lambda), \theta_3(\lambda))(0,0,w_2(\lambda)), \lambda \in \Lambda_c, \quad (24)$$

The local width of the slit is thus given by $w_1(\lambda)+w_2(\lambda)$. It will be seen further below that a constant width collimator slit with $$w_1(\lambda) = w_2(\lambda) = \frac{r_s - r_c}{r_s + r_d}(l_b/2) \quad (25)$$

is a good choice.

At a given point in time during a scan, the x-ray tube emits a cone beam of x-rays from the current source point of the target ring towards to the opposite detector strip. A segment of the detector strip is activated and measures the intensity of the x-rays impinging on it. The segment is made long enough to avoid a transverse truncation of the projection being measured. For example, when the parameters $r_s$, $r_d$, and $w_d$ are chosen as $r_s$=900 mm, $r_d$=675 mm, and $w_d$=40 mm, then the active segment of the cone beam may be made 19 detector modules long, in which case the resulting transverse cone angle is about 30°. To obtain transversely non-truncated cone beam projections even with those cone beams that start near an end of the target ring, the angular span of the detector strip needs to be extended. This is the reason for making the interval $\Lambda_d$ a little wider than the interval $\Lambda_s$. The worst case occurs with those cone beams that start exactly at an end of the target ring. Ideally, the required extension there would be the equivalent of half a transverse cone angle. Extending the detector strip by so much would lead to a self-blocking source/detector arrangement. It may be better to instead accept a reduced transverse cone angle of cone beams that start near an end of the target ring. With non-obese patients, owing to their roughly elliptical cross-section, the cone beam projections near the ends of the target ring will not be transversely truncated even then. For example, with the above values of the parameters $r_s$, $r_d$, and $w_d$, the active segment of the cone beam may be made only 14 detector modules long. The collimator slit should be long enough not to decrease the transverse cone angle any further. This is the reason for making the interval $\Lambda_c$ a little wider than the interval $\Lambda_s$.

The purpose of the collimator slit is to confine the cone beams axially. Ideally, the slit should let pass only those x-rays that will reach the active segment of the detector strip, if not absorbed or scattered. Such an ideal solution is not possible with a rigid collimator slit. However, a good solution is provided by a rigid, constant width collimator slit as defined by (22)-(25). This choice ensures that each cone beam has the ideal axial cone angle at least in the middle of each active segment of the detector strip.

Each module 32 of the detector arrangement 28 may be equipped with an anti-scatter grid. According to an exemplary embodiment of the present invention, the anti-scatter grid is focused onto that point on the target ring that is opposite to the detector module to which the respective anti-scatter grid is attached. Owing to the isocentric design of the source/detector arrangement, the same detector grid may be used for all modules 32 of the detector 28.

According to another exemplary embodiment of the present invention, the detector modules may be orientated such that the long edges of their sensitive areas are parallel to the long axis of the scanner and that the lines that emanate perpendicularly from the center points of their sensitive areas intersect that axis. Such an arrangement advantageously allows for a simplified packing of the detector modules. However, in such a case the anti-scatter grids have to be differently focused for each detector module.

Alternatively, the detector arrangement 28 may be placed on the surface of a cylinder about the long axis of the scanner. Advantageously, the target ring and the collimator slit are then confined to cylindrical surfaces too. Such an arrangement would also simplify the packing of the detector modules. Again also, it would necessitate differently focused anti-scatter grids for each of the detector modules.

The invention claimed is:

1. A computed tomography apparatus, comprising:
   a source of radiation for generating a cone beam of radiation penetrating a volume of interest around an isocenter such that the cone beam is emitted from a first location; and
   a radiation detector; wherein the source of radiation is adapted such that the first location is displaceable along a first trajectory; wherein the radiation detector extends along a second trajectory; wherein the first trajectory is complete with respect to a sizeable volume around the isocenter; wherein completeness is defined as the set of all planes which intersect both the first trajectory and the sizeable volume around the isocenter; wherein the first and second trajectories are such that a straight line that starts at a point on the first trajectory and passes through the isocenter intersects the second trajectory; and wherein the cone beam that is emitted from the first location is not significantly blocked by a portion of the radiation detector between the first trajectory and the volume of interest.

2. The computed tomography apparatus of claim 1, wherein the source of radiation comprises: an electron source for generating an electron beam; and a target ring; wherein the electron source is adapted such that the electron beam is at least partially focused at the target ring; wherein the electron source is adapted such that the electron beam hits the target ring at the a first location which is displaceable along at least a portion of the target ring; and wherein the target ring extends along the first trajectory.

3. The computed tomography apparatus of claim 2, wherein a collimator slit is provided essentially parallel to the target ring.

4. The computed tomography apparatus of claim 3, wherein the cone beam passes through the collimator slit to intersect the volume of interest, wherein the collimator slit is a constant width to prevent a truncated cone beam.

5. The computed tomography apparatus of claim 4, wherein the collimator slit is located along a trajectory which is a scaled image of the first trajectory.

6. The computed tomography apparatus of claim 1, wherein the cone beam of radiation is a cone beam of x-rays.

7. The computed tomography apparatus of claim 1, wherein the radiation detector comprises a plurality of two dimensional detector modules; wherein the plurality of two dimensional detector modules are arranged side by side; wherein the plurality of two dimensional detector modules comprises first detector modules and second detector modules; wherein the first and second detector modules are arranged alternately; wherein the first detector modules are arranged at a first distance from a first center of a volume of interest; and wherein the second detector modules are arranged at a second distance from the first center of the volume of interest.

8. The computed tomography apparatus of claim 1, wherein the first trajectory extends on the surface of a first sphere having a first center and a first radius; wherein the second trajectory extends on the surface of a second sphere having the first center and a second radius; and wherein the first radius is different than the second radius.

9. The apparatus of claim 1, wherein the first trajectory is complete with respect to a volume, a three-dimensional image of the content of the volume may be reconstructed from non-truncated cone beam projections.

10. The apparatus of claim 1, wherein the sizeable volume around the isocenter is chosen as the largest volume with respect to which the first trajectory is complete.

11. Method of operating a computed tomography apparatus, the method comprising the steps of: providing a source of radiation for generating a cone beam of radiation such that the cone beam is emitted from a first location and penetrates a volume of interest around an isocenter; providing a radiation detector which extends along a second trajectory; operating the source of radiation such that the first location is displaced along a first trajectory; wherein the first trajectory is complete with respect to a sizeable volume around the isocenter; wherein the first trajectory and the sizeable volume around the isocenter have finite boundaries that define three-dimensional volumes; wherein completeness occurs for the set of all planes that intersects both the first trajectory and the sizeable volume around the isocenter; wherein the first and second trajectories are such that a straight line that starts at a point on the first trajectory and passes through the volume of interest around the isocenter intersects the second trajectory; and wherein the cone beam that is emitted from the first location is not significantly blocked by a portion of the radiation detector between the first trajectory and the volume of interest around the isocenter.

12. The method of claim 11, further comprising the steps of: providing the source of radiation with a target ring and an electron source for generating an electron beam; at least partially focusing the electron beam at the target ring which is extends along the first trajectory; operating the electron source such that the electron beam hits the target ring at the first location such that the first location is displaced along at least a portion of the target ring.

13. The method of claim 11, wherein the second trajectory is a scaled mirror image of the first trajectory; and wherein the first trajectory and the second trajectory are not equal.

14. The method of claim 11, wherein the radiation detector extending along the second trajectory comprises:
detector modules being placed along the second trajectory according to detector brick $B(\lambda)$ locations; wherein a first brick $B(\lambda_0)$ is placed such that a second brick $B(\lambda_1)$ with $\lambda_1 > \lambda_0$ just touches the first brick, with a continuing sequence $\lambda_0 < \lambda_1 < \lambda_M \leq 1+\epsilon_d$, with $0 \leq \epsilon_d \leq \epsilon$ such that $B(\lambda_m)$ just touches $B(\lambda_{m-1})$ for m=1, 2, ... M and no $\lambda_{M+1}$ can be found such that $\lambda_{M+1} \leq 1+\epsilon_d$ and $B(\lambda_M)$ just touches $B(\lambda_{M-1})$; wherein the detector bricks are not parallel; wherein $\lambda E \Lambda$; wherein $\Lambda[-\epsilon, 1+\epsilon]$; wherein $\epsilon \geq 0$.

15. The method of claim 11, wherein the sensitive area of each radiation detector module faces the isocenter such that a straight line that starts at the radiation detector module face and passes through the isocenter intersects the first trajectory.

16. The method of claim 11, wherein a segment of the radiation detector is activated to measure the intensity of the cone beam impinging on it; wherein the segment activated is made long enough to avoid a transverse truncation of the projection being measured; and wherein the angular span of the radiation detector is extended to obtain transversely non-truncated projections for those cone beams that start near an end of the target ring.

17. The method of claim 11, wherein a rigid, constant width collimator slit is provided to confine the cone beams axially, wherein the confined cone beam angle along the axial direction is symmetrical.

18. The method of claim 11, wherein each module of the radiation detector is equipped with an anti-scatter grid; wherein the anti-scatter grid is focused onto a point on the first trajectory that is opposite the radiation detector module to which the anti-scatter grid is attached.

19. An apparatus for operating a computed tomography apparatus comprising:
wherein the computed tomography apparatus has a source of radiation for generating a cone beam of radiation such that the cone beam penetrating a volume of interest around an isocenter is emitted from a first location and a radiation detector which extends along a second trajectory;
a processor; and
a computer readable storage medium encoded with computer executable instructions which, when executed by the processor, causes the processor to:
operate the source of radiation such that the first location is displaced along a first trajectory; wherein the first trajectory is complete with respect to a sizeable volume around the isocenter; wherein completeness occurs for the set of all planes that intersects both the first trajectory and the sizeable volume around the isocenter; wherein the first trajectory and the sizeable volume around the isocenter have finite boundaries that define three-dimensional volumes; wherein the first and second trajectories are such that a straight line that starts at a point on the first trajectory and passes through the sizeable volume around the isocenter intersects the second trajectory; and wherein the cone beam that is emitted from the first location is not significantly blocked by a portion of the radiation detector between the first trajectory and the sizeable volume around the isocenter.

20. The programmable device of claim 19, wherein the source of radiation comprises: an electron source for generating an electron beam; and a target ring; wherein the electron source is adapted such that the electron beam is at least partially focused at a point on the target ring; wherein the electron source is adapted such that the electron beam hits the first trajectory at the a first location which is displaceable along at least a portion of the target ring; and wherein the target ring extends along the first trajectory.

* * * * *